(12) United States Patent
Gupta et al.

(10) Patent No.: US 9,766,239 B2
(45) Date of Patent: Sep. 19, 2017

(54) SYNBODIES FOR DETECTION OF HUMAN NOROVIRUS

(71) Applicants: Nidhi Gupta, Phoenix, AZ (US); Chris Diehnelt, Chandler, AZ (US); Charles Arntzen, Gold Canyon, AZ (US); Stephen Johnston, Tempe, AZ (US)

(72) Inventors: Nidhi Gupta, Phoenix, AZ (US); Chris Diehnelt, Chandler, AZ (US); Charles Arntzen, Gold Canyon, AZ (US); Stephen Johnston, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 79 days.

(21) Appl. No.: 14/776,434

(22) PCT Filed: Mar. 12, 2014

(86) PCT No.: PCT/US2014/024932
§ 371 (c)(1),
(2) Date: Sep. 14, 2015

(87) PCT Pub. No.: WO2014/195240
PCT Pub. Date: Oct. 9, 2014

(65) Prior Publication Data
US 2016/0153991 A1     Jun. 2, 2016

Related U.S. Application Data

(60) Provisional application No. 61/780,102, filed on Mar. 13, 2013.

(51) Int. Cl.
*C07K 16/08* (2006.01)
*G01N 33/569* (2006.01)
*C07K 14/00* (2006.01)

(52) U.S. Cl.
CPC ..... *G01N 33/56983* (2013.01); *C07K 14/001* (2013.01); *C07K 16/08* (2013.01); *C07K 2318/20* (2013.01); *G01N 2333/08* (2013.01); *G01N 2469/10* (2013.01); *G01N 2800/26* (2013.01)

(58) Field of Classification Search
CPC .......... A61K 38/10; C07K 16/10; C07K 7/06; C07K 7/08; G01N 2333/08; G01N 33/56983
See application file for complete search history.

(56) References Cited

U.S. PATENT DOCUMENTS

2011/0020786 A1   1/2011   Palzkill et al.
2013/0023582 A1   1/2013   Shimamoto et al.

FOREIGN PATENT DOCUMENTS

WO     WO2012134416     * 10/2012     ....... G01N 33/56983

OTHER PUBLICATIONS

Diehnelt, Synbody Ligands for Norovirus Detection and Capture, Nov. 7, 2012. [Retrieved from the Internet Jun. 16, 2014; <http://norocore.ncsu.edu/cms/wp-content/uploads/2012/11/Novel-Ligands-Chris-Diehnelt.pdf>]; p. 4, 7, 8.

* cited by examiner

*Primary Examiner* — Bao Li
(74) *Attorney, Agent, or Firm* — Quarles & Brady LLP; Gavin J. Milczarek-Desai

(57) ABSTRACT

Synbodies specific for Norovirus and coupled with a substrate provide Norovirus binding and detection platforms (FIG. 1). A Norovirus capturing platform, comprising one or more synbodies selected from the group consisting of synbodies 6-6, 92-92, 93-93, and 94-94 coupled to a substrate, has been found to found to bind with either GII.4 Minerva or both GII.4 Minerva and GII.4 Sydney# strains of norovirus.

11 Claims, 8 Drawing Sheets

Scaffold-1571　　　　　　　Scaffold-MAP-2

SYNBODIES FOR DETECTION OF HUMAN NOROVIRUS

CROSS-REFERENCE TO RELATED APPLICATIONS

This Application is a 371 application of PCT/US2014/024932 filed Mar. 12, 2014, which claims benefit of U.S. Provisional Patent Application No. 61/780,102, filed Mar. 13, 2013, which are incorporated herein by reference in their entirety.

STATEMENT REGARDING FEDERALLY SPONSORED RESEARCH

This invention was made with government support under 2011-68003-30395 awarded by U.S. Department of Agriculture/National Institute of Food and Agriculture. The government has certain rights in the invention.

BACKGROUND OF THE INVENTION

Norovirus, a Calicivirus (family Caliciviridae), is colloquially known as "stomach flu" or "food poisoning". Norovirus is recognized as one of the major causes of nonbacterial outbreaks worldwide. This accounts for an estimated of 23 million infections per year in the US (the second highest cause of nonbacterial gastroenteritis (GE) morbidity) and imposes a substantial burden on healthcare.

Norovirus is classified as "NIAID category B Priority bio-defense Pathogen". It is a non-enveloped, single-stranded, positive sense RNA genome which is environmentally stable due to capsid formation. It can resist freezing and heating to up to 60 C and is stable at low concentrations of chlorine. An infectious dose of 10-100 viruses via fecal-oral transmission or droplet transmission can lead to infection. This is a highly contagious but short-lived illness (48 hrs) causes vomiting, stomach pain and diarrhea. Also, it can cause chronic infections in transplant recipient.

Of the five geno-groups of Norovirus, GI, GII, and GIV are known to infect humans. There is no available vaccine for human Norovirus infection, with progress being hampered by the absence of suitable animal model/cell culture for preclinical testing of the candidate vaccine. Presently, the detection of viral RNA is limited to RT-PCR in the stool samples of affected humans.

SUMMARY OF THE INVENTION

The embodiments disclosed herein generally relate to the creation of synbodies for Norovirus and to simple, practical, and broadly reactive methods to detect human Norovirus in relevant non-clinical sample matrices (e.g., food, water, and environment).

These and other aspects of the invention will be apparent upon reference to the following detailed description and figures. To that end, any patent and other documents cited herein are hereby incorporated by reference in their entirety.

DETAILED DESCRIPTION OF THE INVENTION

Embodiments of the invention relate to peptide affinity ligands (synbodies) for the detection of human Norovirus. As a first step to creating a synbody, a virus-like particle (VLP) was used as a Norovirus surrogate. The Norovirus surrogate VLP (nVLP) assembled from capsid structural subunits antigenically resembles native virus yet lacks viral nucleic acid, thereby rendering it non-infectious. The nVLP can be produced in a variety of known prokaryotic and eukaryotic expression systems to provide an ample sample supply.

Figure 1:
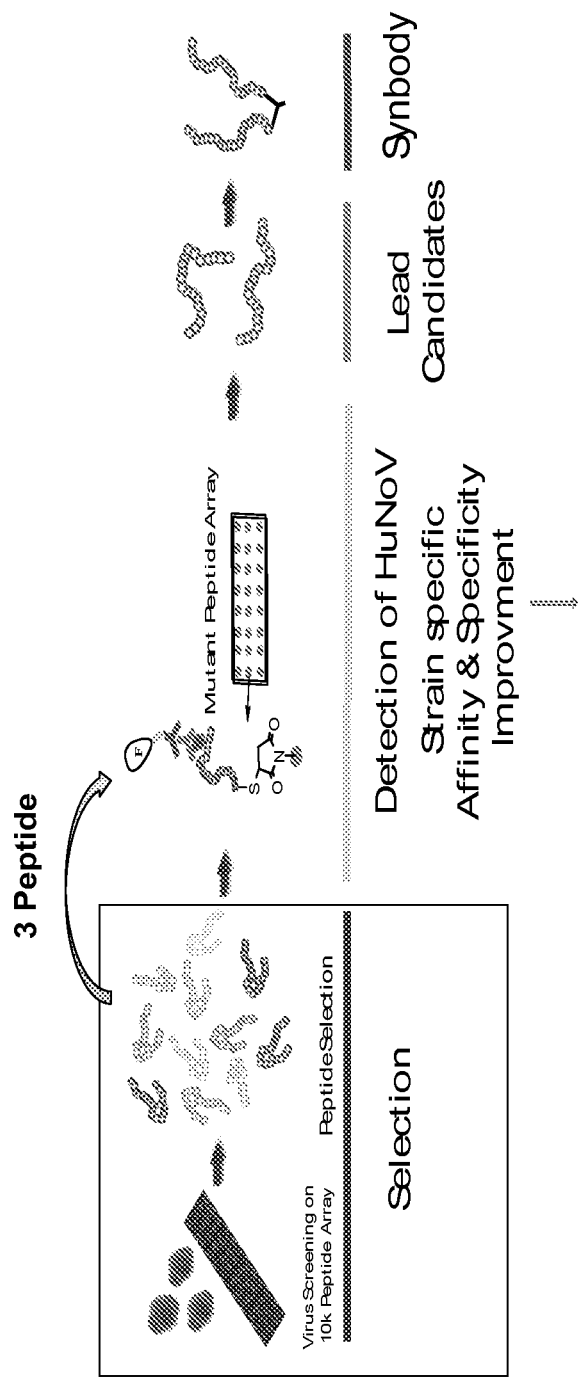
FIG. 1 illustrates an overview of the identification of lead peptide candidates.
Figure 2:
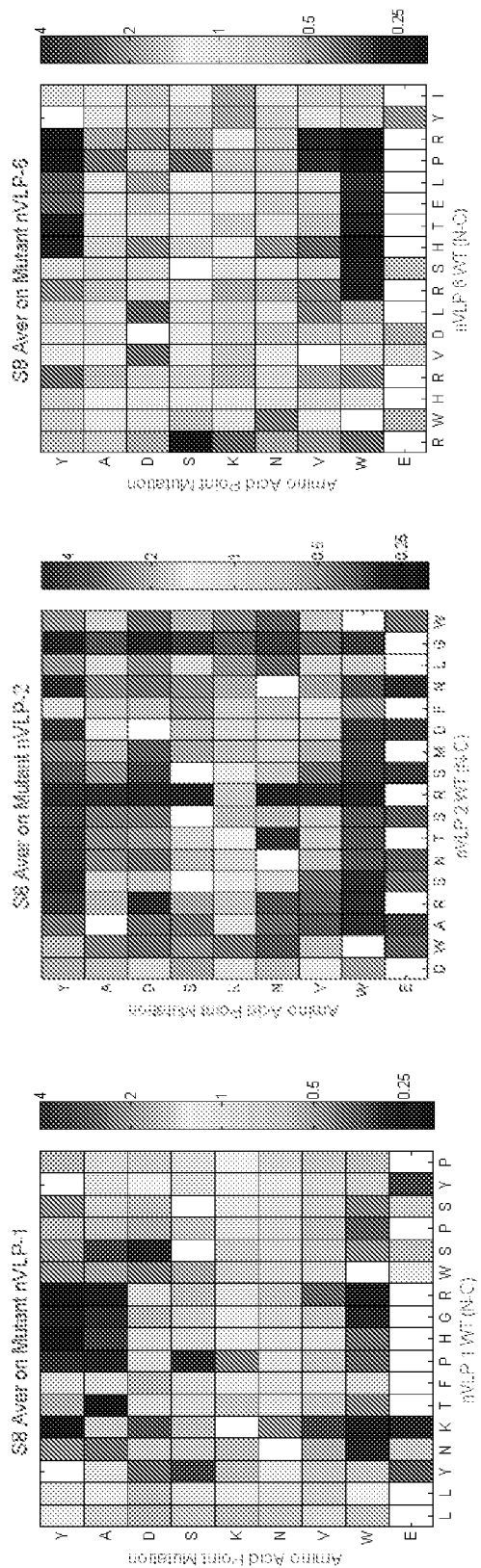
FIG. 2 depicts a heat MAP of the Optimization of lead peptide candidates for nVLP GII.4.

To engineer peptide affinity ligands for nVLP, peptides specific for nVLP were identified by screening cell lysate from baculovirus expression and transgenic tobacco expression of nVLP (type GII.4 Minerva strain) against a library of 10,000 20mer peptides of random sequences in microarray format. Three lead peptides were identified. With an aim to detect very low amount of virus coat protein present in complex mixture, we focused on improving the affinity and specificity of the identified lead peptides for nVLP GII.4 (FIGS. 1 and 2).

For this, nine amino acids (Y, A, D, S, K, N, V, W, E) were selected and an amino acid point variant peptide library for each selected lead peptide was designed. These peptides (408 in all) were printed on microarrays using similar sulfhydryl chemistry as used in the 10,000 peptide microarrays and screened against nVLP GII.4. After amino acid substitutions for increased binding affinity for nVLP GII.4 were identified, a library of optimized peptides (96) was created by the addition of 5-7 amino acid combinations.

Figure 3:
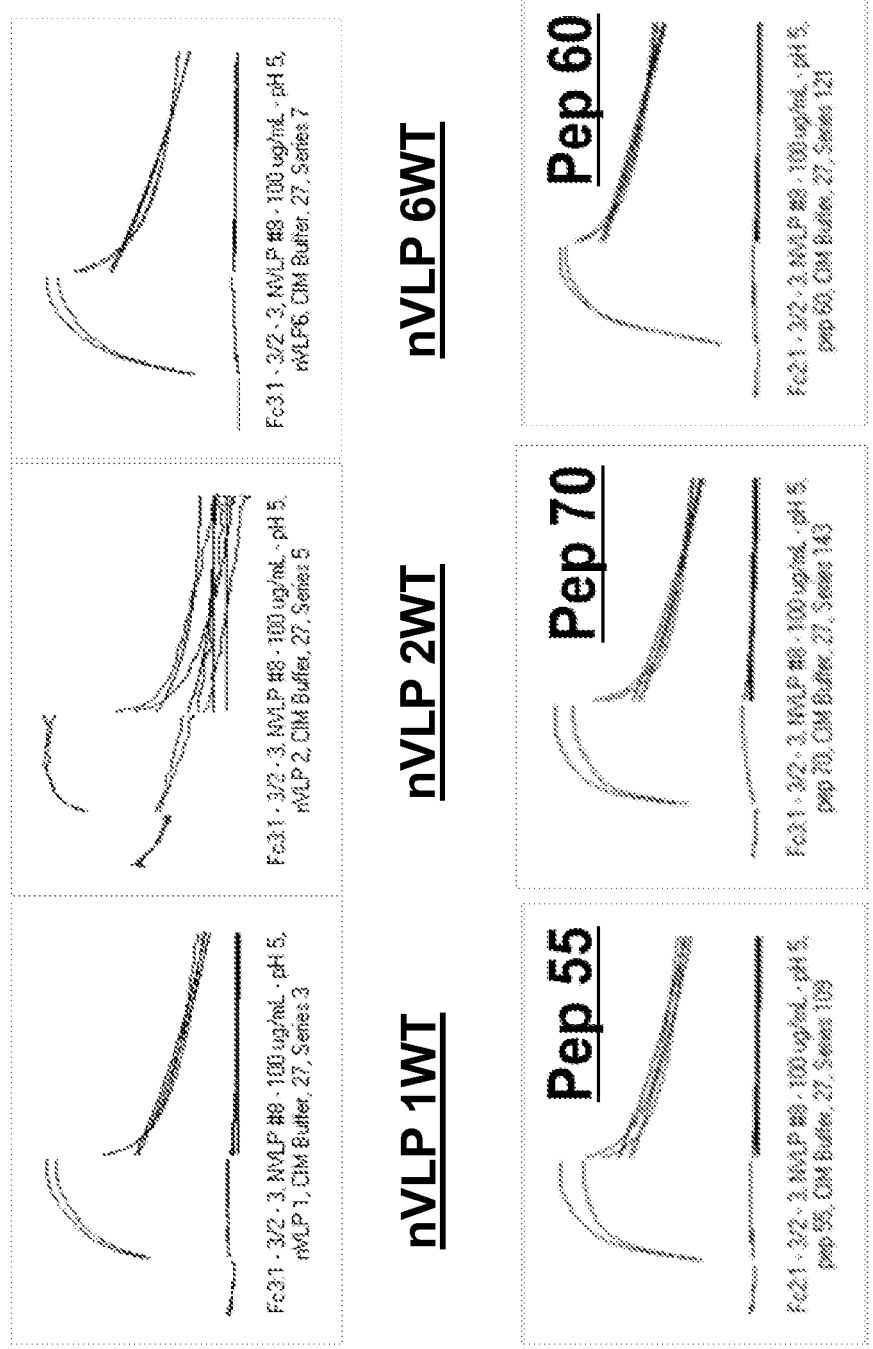
FIG. 3 depicts surface plasmon resonance screening of optimized peptides.

These 96 peptides were synthesized and tested unpurified against GII.4 via surface plasmon resonance (SPR), a sample of which is shown in FIG. 3. Peptides candidates were analyzed and selected for improved binding and slower dissociation rate. Finally, a list of 10 peptide candidates with improved binding and slower dissociation rates were chosen to construct bivalent peptide affinity reagents (synbodies).

TABLE-1

Selected Peptides candidates for Synbody Construction

| SEQ ID NO. | Peptide Code | Selected Peptides | Avg Binding (Spot 1/2) | % Stability | $k_{d\_1}$ (sec) |
|---|---|---|---|---|---|
| 1 | nVLP-1WT | LLYNKTFPHGRWSPSYPGSC | 71.5 | 25% | 7.85E-03 |
| 2 | nVLP-2WT | DWARSNTSRSMDFNLGWGSC | 2.5 | — | 2.33E-02 |
| 3 | Mut Peptide-81 | AWARSNNSRSKAFNLGWGSC | 127.9 | 45% | 4.55E-03 |
| 4 | Mut Peptide-60 | DWARKNNKRKMNFNLGWGSC | 134.3 | 44% | 4.87E-03 |
| 5 | Mut Peptide-53 | VWARKNNKRKKDFNAGWGSC | 188.8 | 51% | 4.08E-03 |
| 6 | Mut Peptide-78 | SWARSNNKRSKAFNLGWGSC | 168.8 | 46% | 4.31E-03 |
| 7 | nVLP-6WT | RWHRVDLRSHTELPRYIGSC | 175.7 | 37% | 5.13E-03 |
| 8 | Mut Peptide-92 | RWHRVKLRSHTELNRYIGSC | 229.5 | 57% | 3.55E-03 |
| 9 | Mut Peptide-93 | RWVRVKLRSHTELNRYIGSC | 274.2 | 60% | 3.32E-03 |
| 10 | Mut Peptide-94 | RWVRVKLRSHTKLRYIGSC | 358.2 | 63% | 2.94E-03 |

Figure 4:
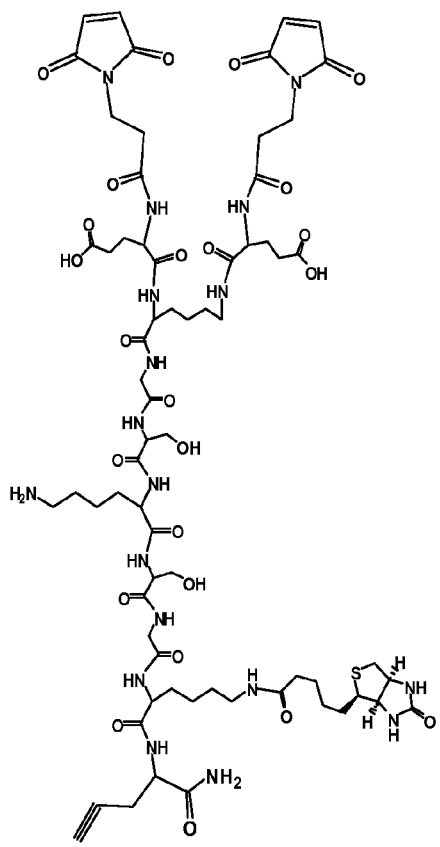
FIG. 4 depicts nVLPGII.4 synbody construction.
Figure 4:
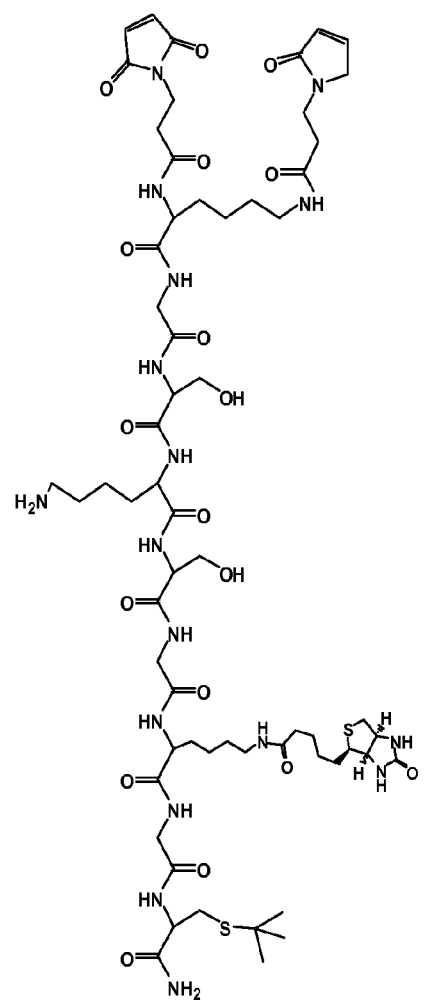
Figure 5:
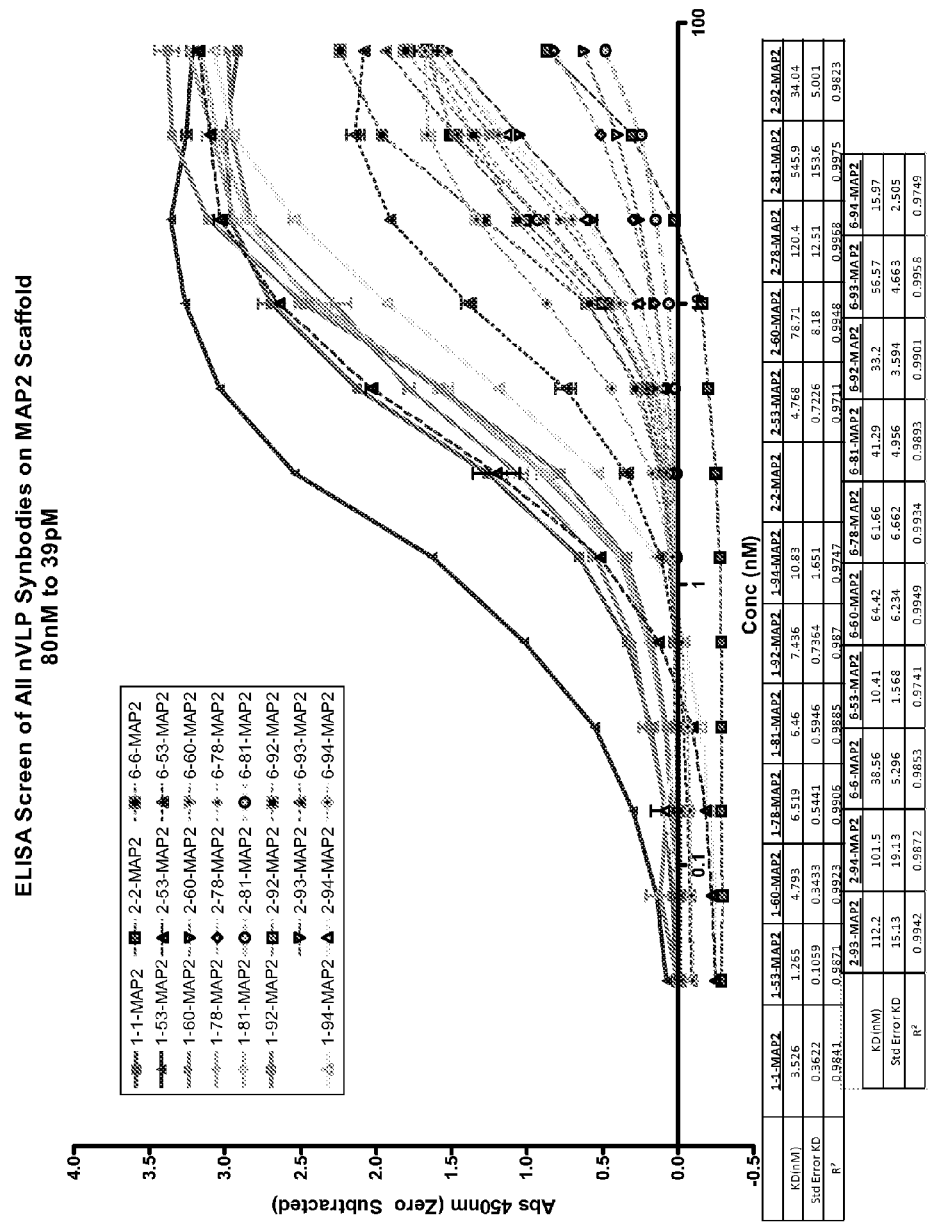
FIG. 5 depicts an ELISA screening of nVLPGII.4 synbodies.
Figure 6:
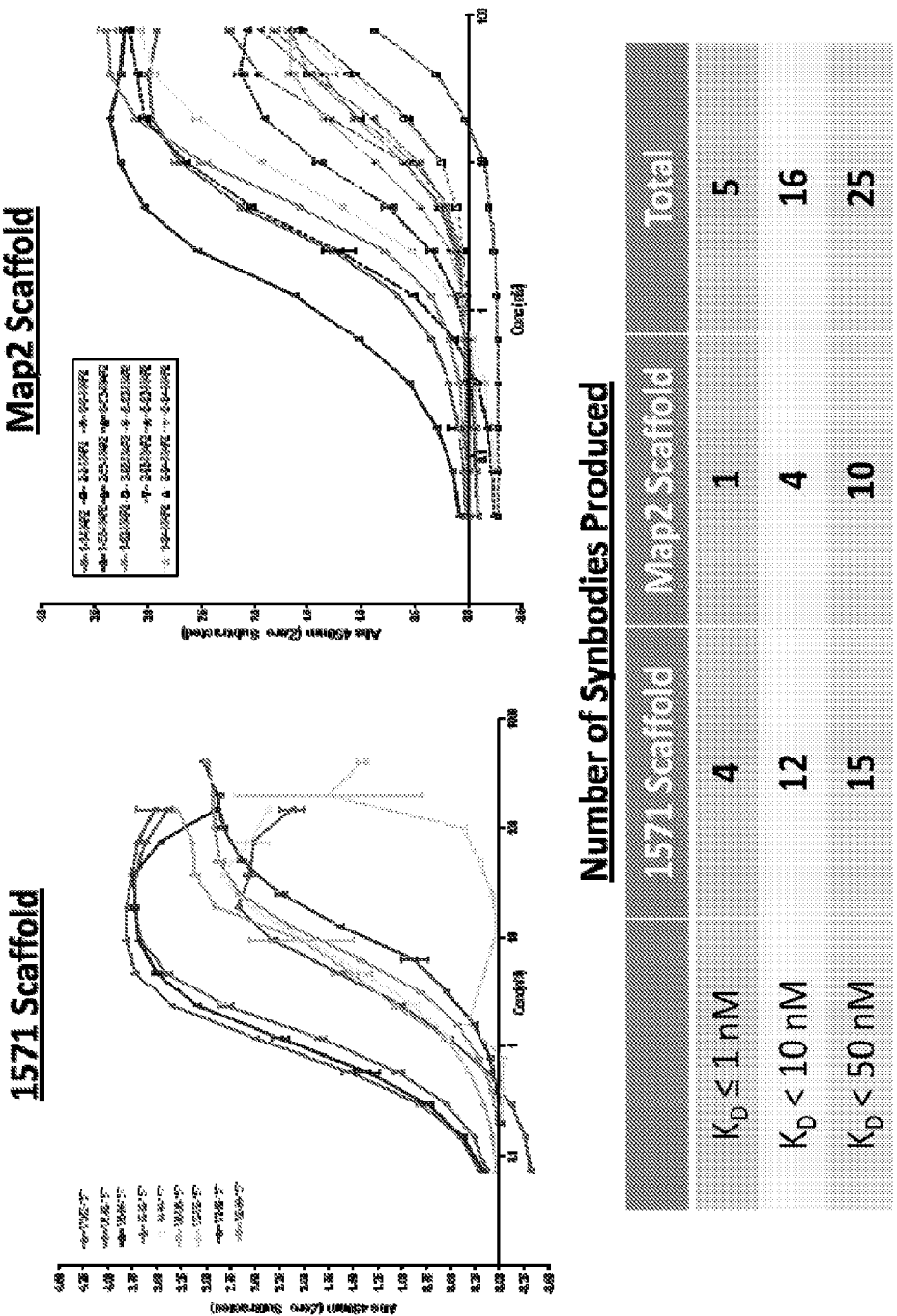
FIG. 6 depicts nVLP (GII.4) synbodies with $K_D<50$ nM.

Construction of Peptide Affinity Reagents (Synbody) for nVLP GII.4:

Two scaffolds (scaffold-1571 and scaffold-MAP-2) with maleimide functional groups were selected for synbody construction (see, for example, FIG. 4). Peptide candidates (Table 1) were constrained on two scaffolds via sulfhydryl coupling. A total of 53 synbody conjugation reactions were carried out on two different scaffold types and 98 synbodies were recovered after HPLC purification. Synbodies were characterized by a matrix-assisted laser desorption/ionization time-of-flight mass spectrometer (MALDI-TOF) and tested against purified GII.4 nVLP binding in a direct ELISA assay (FIG. 5). Table 2 and FIG. 6 show synbodies with $K_D < 50$ nM.

TABLE-2 nVLP (GII.4) Synbodies with $K_D < 50$ nM
nVLP Synbodies for GII.4

| SEQ ID NO. | Synbody | Synbody Sequence | Scaffold | ELISA KD |
|---|---|---|---|---|
| 11 | nVLP6-6-1571 | RWHRVDLRSHTELPRYIGSC-RWHRVDLRSHTELPRYIGSC-1571 | 1571 | 2 nM |
| 12 | nVLP6-53-1571 | RWHRVDLRSHTELPRYIGSC-VWARKNNKRKKDFNAGWGSC-1571 | 1571 | 1 nM |
| 13 | nVLP6-78-1571 | RWHRVDLRSHTELPRYIGSC-SWARSNNKRSKAFNLGWGSC-1571 | 1571 | 2 nM |
| 14 | nVLP6-92-1571 | RWHRVDLRSHTELPRYIGSC-RWHRVKLRSHTELNRYIGSC-1571 | 1571 | 2 nM |
| 15 | nVLP6-60-1571 | RWHRVDLRSHTELPRYIGSC-DWARKNNKRKMNFNLGWGSC-1571 | 1571 | 3 nM |
| 16 | nVLP6-81-1571 | RWHRVDLRSHTELPRYIGSC-RWHRVDLRSHTELPRYIGSC-1571 | 1571 | 3 nM |
| 17 | nVLP6-94-1571 | RWHRVDLRSHTELPRYIGSC-RWHRVDLRSHTELPRYIGSC-1571 | 1571 | 1 nM |
| 18 | nVLP2-53-1571 | DWARSNTSRSMDFNLGWGSC-VWARKNNKRKKDFNAGWGSC-1571 | 1571 | 20 nM |
| 19 | nVLP2-78-1571 | DWARSNTSRSMDFNLGWGSC-SWARSNNKRSKAFNLGWGSC-1571 | 1571 | 25 nM |
| 20 | nVLP2-92-1571 | DWARSNTSRSMDFNLGWGSC-RWHRVKLRSHTELNRYIGSC-1571 | 1571 | 15 nM |
| 21 | nVLP2-60-1571 | DWARSNTSRSMDFNLGWGSC-DWARKNNKRKMNFNLGWGSC-1571 | 1571 | 10 nM |
| 22 | nVLP2-81-1571 | DWARSNTSRSMDFNLGWGSC-AWARSNNSRSKAFNLGWGSC-1571 | 1571 | 40 nM |
| 23 | nVLP2-92-1571 | DWARSNTSRSMDFNLGWGSC-RWHRVKLRSHTELNRYIGSC- |  | 10 nM |
| 24 | nVLP2-93-1571 | DWARSNTSRSMDFNLGWGSC-RWVRVKLRSHTELNRYIGSC- |  | 5 nM |
| 25 | nVLP2-94-1571 | DWARSNTSRSMDFNLGWGSC-RWVRVKLRSHTKLRYIGSC-1571 | 1571 | 5 nM |
| 26 | nVLP1-53-1571 | LLYNKTFPHGRWSPSYPGSC-VWARKNNKRKKDFNAGWGSC-1571 | 1571 | 19 nM |
| 27 | nVLP1-55-1571 | LLYNKTFPHGRWSPSYPGSC-VWARKNNSRSKDFNAGWGSC-1571 | 1571 | 7 nM |

TABLE-2 -continued nVLP (GII.4) Synbodies with $K_D$ < 50 nM
nVLP Synbodies for GII.4

| SEQ ID NO. | Synbody | Synbody Sequence | Scaffold | ELISA KD |
|---|---|---|---|---|
| 28 | nVLP1-72-1571 | LLYNKTFPHGRWSPSYPGSC-SWARSNNSRSMDFNLGWGSC-1571 | 1571 | 15 nM |
| 29 | nVLP1-93-1571 | LLYNKTFPHGRWSPSYPGSC-RWVRVKLRSHTELNRYIGSC-1571 | 1571 | 4 nM |
| 30 | nVLP1-94-1571 | LLYNKTFPHGRWSPSYPGSC-RWVRVKLRSHTKLNRYIGSC-1571 | 1571 | 6 nM |
| 31 | nVLP60-60-1571 | DWARKNNKRKMNFNLGWGSC-DWARKNNKRKMNFNLGWGSC-1571 | 1571 | 2 nM |
| 32 | nVLP81-81-1571 | AWARSNNSRSKAFNLGWGSC-AWARSNNSRSKAFNLGWGSC-1571 | 1571 | 3 nM |
| 33 | nVLP93-93-1571 | RWVRVKLRSHTELNRYIGSC-RWVRVKLRSHTELNRYIGSC-1571 | 1571 | 4 nM |
| 34 | nVLP78-78-1571 | SWARSNNKRSKAFNLGWGSC-SWARSNNKRSKAFNLGWGSC-1571 | 1571 | 5 nM |
| 35 | nVLP92-92-1571 | RWHRVKLRSHTELNRYIGSC-RWHRVKLRSHTELNRYIGSC-1571 | 1571 | 3 nM |
| 36 | nVLP94-94-1571 | RWVRVKLRSHTKLNRYIGSC-RWVRVKLRSHTKLNRYIGSC-1571 | 1571 | 1 nM |
| 37 | nVLP53-53-1571 | VWARKNNKRKKDFNAGWGSC-VWARKNNKRKKDFNAGWGSC-1571 | 1571 | 1 nM |
| 38 | nVLP55-55-1571 | VWARKNNSRSKDFNAGWGSC-VWARKNNSRSKDFNAGWGSC-1571 | 1571 | 9 nM |
| 39 | nVLP1-1-MAP2 | LLYNKTFPHGRWSPSYPGSC-LLYNKTFPHGRWSPSYPGSC-MAP2 | MAP-2 | 4 nM |
| 40 | nVLP1-53-MAP2 | LLYNKTFPHGRWSPSYPGSC-LLYNKTFPHGRWSPSYPGSC-MAP2 | MAP-2 | 2 nM |
| 41 | nVLP1-60-MAP2 | LLYNKTFPHGRWSPSYPGSC-LLYNKTFPHGRWSPSYPGSC-MAP2 | MAP-2 | 5 nM |
| 42 | nVLP1-78-MAP2 | LLYNKTFPHGRWSPSYPGSC-LLYNKTFPHGRWSPSYPGSC-MAP2 | MAP-2 | 7 nM |
| 43 | nVLP1-81-MAP2 | LLYNKTFPHGRWSPSYPGSC-LLYNKTFPHGRWSPSYPGSC-MAP2 | MAP-2 | 7 nM |
| 44 | nVLP1-92-MAP2 | LLYNKTFPHGRWSPSYPGSC-LLYNKTFPHGRWSPSYPGSC-MAP2 | MAP-2 | 8 nM |
| 45 | nVLP1-94-MAP2 | LLYNKTFPHGRWSPSYPGSC-LLYNKTFPHGRWSPSYPGSC-MAP2 | MAP-2 | 1 nM |
| 46 | nVLP2-53-MAP2 | DWARSNTSRSMDFNLGWGSC-VWARKNNKRKKDFNAGWGSC-MAP2 | MAP-2 | 5 nM |
| 47 | nVLP2-92-MAP2 | DWARSNTSRSMDFNLGWGSC-RWHRVKLRSHTELNRYIGSC-MAP2 | MAP-2 | 34 nM |
| 48 | nVLP6-6MAP2 | RWHRVDLRSHTELPRYIGSC-RWHRVDLRSHTELPRYIGSC-MAP2 | MAP-2 | 39 nM |
| 49 | nVLP6-53-MAP2 | RWHRVDLRSHTELPRYIGSC-VWARKNNKRKKDFNAGWGSC-MAP2 | MAP-2 | 0 nM |
| 50 | nVLP6-81-MAP2 | RWHRVDLRSHTELPRYIGSC-AWARSNNSRSKAFNLGWGSC-MAP2 | MAP-2 | 40 nM |
| 51 | nVLP6-92-MAP2 | RWHRVDLRSHTELPRYIGSC-RWHRVKLRSHTELNRYIGSC-MAP2 | MAP-2 | 33 nM |
| 52 | nVLP6-93-MAP2 | RWHRVDLRSHTELPRYIGSC-RWVRVKLRSHTELNRYIGSC-MAP2 | MAP-2 | 50 nM |

ELISA Detection.

Figure 7:
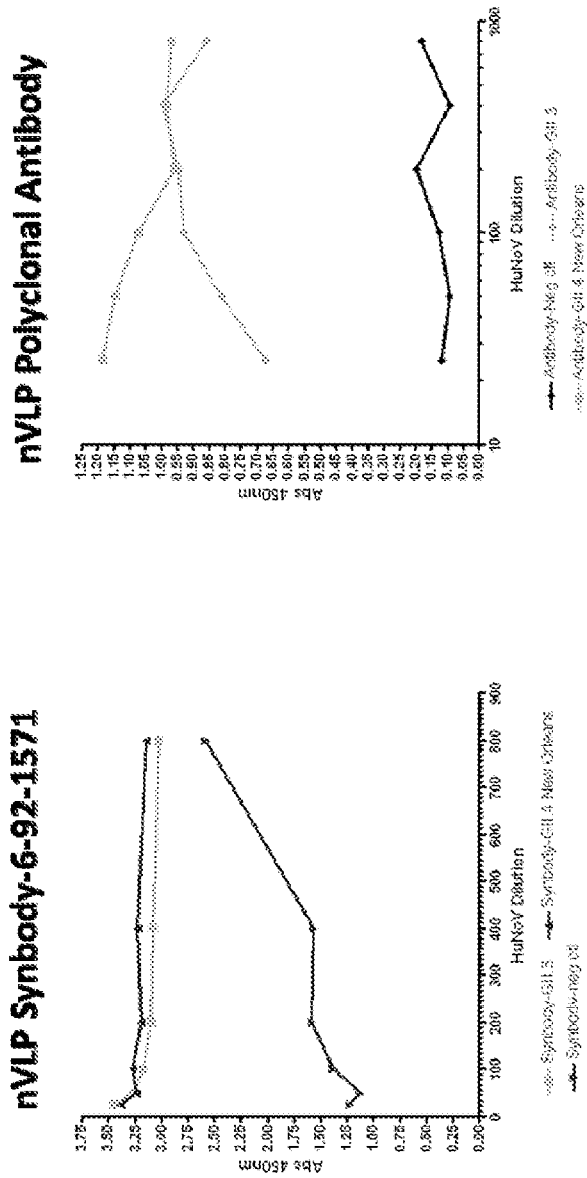
FIG. 7 depicts the ELISA based detection of human Norovirus.

A direct ELISA method for detection of HuNoV also has been developed. Stool samples containing HuNoV (GII.3, GII.4, or no NoV) were coated onto an ELISA plate and detected with a fixed concentration of the candidate synbody. Initial results clearly indicate that the synbody performs similarly to a polyclonal antibody raised against the GII.4 strain (FIG. 7).

Figure 8:
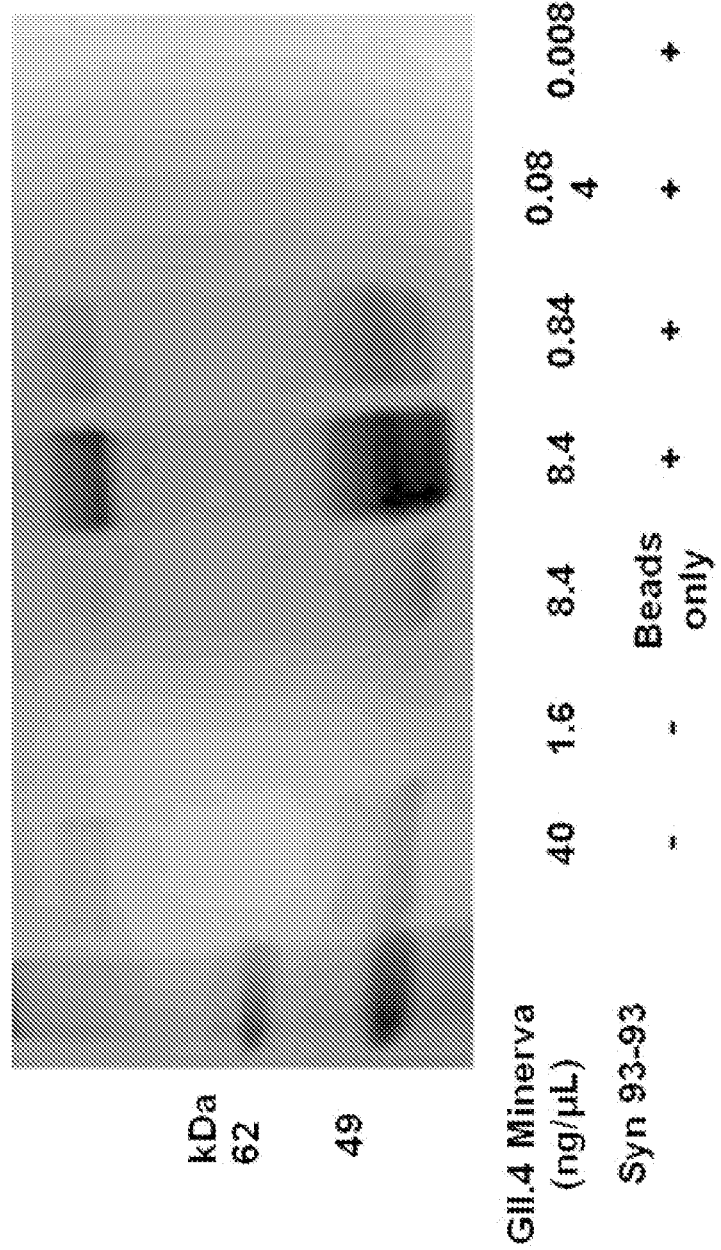
FIG. 8 depicts the enrichment of GII.4 Minerva VLP captured from a dilute solution using synbody 93-93.

As shown in FIG. 8 and Table 3, enrichment of either GII.4 Minerva or both GII.4 Minerva and GII.4 Sydney# occurs for synbodies 6-6, 92-92, 93-93, and 94-94 from Table 2.

TABLE 3

Enrichment of two different Norovirus VLPs captured from a dilute solution.

| VP1 Protein | Enrichment Factor from 1 ng/µL solution | | | |
|---|---|---|---|---|
| Identity | Syn 6-6 | Syn 92-92 | Syn 93-93 | Syn 94-94 |
| GII.4 Minerva | 100% | 16 | 3 | 10 | 7 |
| GII.4 Sydney# | 95% | n.e. | n.e. | 3 | 3 |

In view of the above, a series of affinity agents for the detection of Norovirus have been developed. These synbodies can be used for detection of Norovirus or in capture assays for Norovirus concentration or enrichment. These Norovirus detecting synbodies can be coupled with filtration procedures, which may be used to remove low levels of viruses present in naturally contaminated surfaces or samples.

The claims are not intended to be limited to the embodiments and examples described herein.

The invention claimed is:

1. A norovirus detection agent selected from the group consisting of synbodies 6-6 (SEQ ID NO:11), 92-92 (SEQ ID NO:35), 93-93 (SEQ ID NO:33), and 94-94 (SEQ ID NO:36).

2. A Norovirus capturing platform, comprising one or more synbodies selected from the group consisting of synbodies 6-6 (SEQ ID NO:11), 92-92 (SEQ ID NO:35), 93-93 (SEQ ID NO:33), and 94-94 (SEQ ID NO:36) coupled to a substrate.

3. A method for binding Norovirus, comprising the steps of coupling one or more synbodies of claim 1 to a substrate and contacting said substrate with a sample.

4. The norovirus detection agent of claim 1, wherein said agent is synbody 6-6 (SEQ ID NO:11).

5. The norovirus detection agent of claim 1, wherein said agent is synbody 92-92 (SEQ ID NO:35).

6. The norovirus detection agent of claim 1, wherein said agent is synbody 93-93 (SEQ ID NO:33).

7. The norovirus detection agent of claim 1, wherein said agent is synbody 94-94 (SEQ ID NO:36).

8. The method for binding Norovirus of claim 3, wherein said agent is synbody 6-6 (SEQ ID NO:11).

9. The method for binding Norovirus of claim 3, wherein said agent is synbody 92-92 (SEQ ID NO:35).

10. The method for binding Norovirus of claim 3, wherein said agent is synbody 93-93 (SEQ ID NO:33).

11. The method for binding Norovirus of claim 3, wherein said agent synbody 94-94 (SEQ ID NO:36).

* * * * *

SEQUENCE LISTING

```
<160> NUMBER OF SEQ ID NOS: 52

<210> SEQ ID NO 1
<211> LENGTH: 20
<212> TYPE: PRT
<213> ORGANISM: Artificial sequence
<220> FEATURE:
<223> OTHER INFORMATION: Synthetic

<400> SEQUENCE: 1

Leu Leu Tyr Asn Lys Thr Phe Pro His Gly Arg Trp Ser Pro Ser Tyr
1               5                   10                  15

Pro Gly Ser Cys
            20

<210> SEQ ID NO 2
<211> LENGTH: 20
<212> TYPE: PRT
<213> ORGANISM: Artificial sequence
<220> FEATURE:
<223> OTHER INFORMATION: SYNTHETIC

<400> SEQUENCE: 2

Asp Trp Ala Arg Ser Asn Thr Ser Arg Ser Met Asp Phe Asn Leu Gly
1               5                   10                  15

Trp Gly Ser Cys
            20

<210> SEQ ID NO 3
<211> LENGTH: 20
<212> TYPE: PRT
<213> ORGANISM: Artificial sequence
<220> FEATURE:
<223> OTHER INFORMATION: SYNTHETIC

<400> SEQUENCE: 3

Ala Trp Ala Arg Ser Asn Asn Ser Arg Ser Lys Ala Phe Asn Leu Gly
1               5                   10                  15

Trp Gly Ser Cys
            20
```

```
<210> SEQ ID NO 4
<211> LENGTH: 20
<212> TYPE: PRT
<213> ORGANISM: Artificial sequence
<220> FEATURE:
<223> OTHER INFORMATION: SYNTHETIC

<400> SEQUENCE: 4

Asp Trp Ala Arg Lys Asn Asn Lys Arg Lys Met Asn Phe Asn Leu Gly
1               5                   10                  15

Trp Gly Ser Cys
            20

<210> SEQ ID NO 5
<211> LENGTH: 20
<212> TYPE: PRT
<213> ORGANISM: Artificial sequence
<220> FEATURE:
<223> OTHER INFORMATION: SYNTHETIC

<400> SEQUENCE: 5

Val Trp Ala Arg Lys Asn Asn Lys Arg Lys Lys Asp Phe Asn Ala Gly
1               5                   10                  15

Trp Gly Ser Cys
            20

<210> SEQ ID NO 6
<211> LENGTH: 20
<212> TYPE: PRT
<213> ORGANISM: Artificial sequence
<220> FEATURE:
<223> OTHER INFORMATION: SYNTHETIC

<400> SEQUENCE: 6

Ser Trp Ala Arg Ser Asn Asn Lys Arg Ser Lys Ala Phe Asn Leu Gly
1               5                   10                  15

Trp Gly Ser Cys
            20

<210> SEQ ID NO 7
<211> LENGTH: 20
<212> TYPE: PRT
<213> ORGANISM: Artificial sequence
<220> FEATURE:
<223> OTHER INFORMATION: SYNTHETIC

<400> SEQUENCE: 7

Arg Trp His Arg Val Asp Leu Arg Ser His Thr Glu Leu Pro Arg Tyr
1               5                   10                  15

Ile Gly Ser Cys
            20

<210> SEQ ID NO 8
<211> LENGTH: 20
<212> TYPE: PRT
<213> ORGANISM: Artificial sequence
<220> FEATURE:
<223> OTHER INFORMATION: SYNTHETIC

<400> SEQUENCE: 8

Arg Trp His Arg Val Lys Leu Arg Ser His Thr Glu Leu Asn Arg Tyr
1               5                   10                  15

Ile Gly Ser Cys
```

```
                        20

<210> SEQ ID NO 9
<211> LENGTH: 20
<212> TYPE: PRT
<213> ORGANISM: Artificial sequence
<220> FEATURE:
<223> OTHER INFORMATION: SYNTHETIC

<400> SEQUENCE: 9

Arg Trp Val Arg Val Lys Leu Arg Ser His Thr Glu Leu Asn Arg Tyr
1               5                   10                  15

Ile Gly Ser Cys
            20

<210> SEQ ID NO 10
<211> LENGTH: 20
<212> TYPE: PRT
<213> ORGANISM: Artificial sequence
<220> FEATURE:
<223> OTHER INFORMATION: SYNTHETIC

<400> SEQUENCE: 10

Arg Trp Val Arg Val Lys Leu Arg Ser His Thr Lys Leu Asn Arg Tyr
1               5                   10                  15

Ile Gly Ser Cys
            20

<210> SEQ ID NO 11
<211> LENGTH: 40
<212> TYPE: PRT
<213> ORGANISM: Artificial sequence
<220> FEATURE:
<223> OTHER INFORMATION: SYNTHETIC

<400> SEQUENCE: 11

Arg Trp His Arg Val Asp Leu Arg Ser His Thr Glu Leu Pro Arg Tyr
1               5                   10                  15

Ile Gly Ser Cys Arg Trp His Arg Val Asp Leu Arg Ser His Thr Glu
            20                  25                  30

Leu Pro Arg Tyr Ile Gly Ser Cys
        35                  40

<210> SEQ ID NO 12
<211> LENGTH: 40
<212> TYPE: PRT
<213> ORGANISM: Artificial sequence
<220> FEATURE:
<223> OTHER INFORMATION: SYNTHETIC

<400> SEQUENCE: 12

Arg Trp His Arg Val Asp Leu Arg Ser His Thr Glu Leu Pro Arg Tyr
1               5                   10                  15

Ile Gly Ser Cys Val Trp Ala Arg Lys Asn Asn Lys Arg Lys Lys Asp
            20                  25                  30

Phe Asn Ala Gly Trp Gly Ser Cys
        35                  40

<210> SEQ ID NO 13
<211> LENGTH: 40
<212> TYPE: PRT
<213> ORGANISM: Artificial sequence
<220> FEATURE:
<223> OTHER INFORMATION: SYNTHETIC
```

<400> SEQUENCE: 13

Arg Trp His Arg Val Asp Leu Arg Ser His Thr Glu Leu Pro Arg Tyr
1               5                   10                  15

Ile Gly Ser Cys Ser Trp Ala Arg Ser Asn Asn Lys Arg Ser Lys Ala
            20                  25                  30

Phe Asn Leu Gly Trp Gly Ser Cys
        35                  40

<210> SEQ ID NO 14
<211> LENGTH: 40
<212> TYPE: PRT
<213> ORGANISM: Artificial sequence
<220> FEATURE:
<223> OTHER INFORMATION: SYNTHETIC

<400> SEQUENCE: 14

Arg Trp His Arg Val Asp Leu Arg Ser His Thr Glu Leu Pro Arg Tyr
1               5                   10                  15

Ile Gly Ser Cys Arg Trp His Arg Val Lys Leu Arg Ser His Thr Glu
            20                  25                  30

Leu Asn Arg Tyr Ile Gly Ser Cys
        35                  40

<210> SEQ ID NO 15
<211> LENGTH: 40
<212> TYPE: PRT
<213> ORGANISM: Artificial sequence
<220> FEATURE:
<223> OTHER INFORMATION: SYNTHETIC

<400> SEQUENCE: 15

Arg Trp His Arg Val Asp Leu Arg Ser His Thr Glu Leu Pro Arg Tyr
1               5                   10                  15

Ile Gly Ser Cys Asp Trp Ala Arg Lys Asn Asn Lys Arg Lys Met Asn
            20                  25                  30

Phe Asn Leu Gly Trp Gly Ser Cys
        35                  40

<210> SEQ ID NO 16
<211> LENGTH: 40
<212> TYPE: PRT
<213> ORGANISM: Artificial sequence
<220> FEATURE:
<223> OTHER INFORMATION: SYNTHETIC

<400> SEQUENCE: 16

Arg Trp His Arg Val Asp Leu Arg Ser His Thr Glu Leu Pro Arg Tyr
1               5                   10                  15

Ile Gly Ser Cys Arg Trp His Arg Val Asp Leu Arg Ser His Thr Glu
            20                  25                  30

Leu Pro Arg Tyr Ile Gly Ser Cys
        35                  40

<210> SEQ ID NO 17
<211> LENGTH: 40
<212> TYPE: PRT
<213> ORGANISM: Artificial sequence
<220> FEATURE:
<223> OTHER INFORMATION: SYNTHETIC

<400> SEQUENCE: 17

```
Arg Trp His Arg Val Asp Leu Arg Ser His Thr Glu Leu Pro Arg Tyr
1               5                   10                  15

Ile Gly Ser Cys Arg Trp His Arg Val Asp Leu Arg Ser His Thr Glu
                20                  25                  30

Leu Pro Arg Tyr Ile Gly Ser Cys
            35                  40
```

<210> SEQ ID NO 18
<211> LENGTH: 40
<212> TYPE: PRT
<213> ORGANISM: Artificial sequence
<220> FEATURE:
<223> OTHER INFORMATION: SYNTHETIC

<400> SEQUENCE: 18

```
Asp Trp Ala Arg Ser Asn Thr Ser Arg Ser Met Asp Phe Asn Leu Gly
1               5                   10                  15

Trp Gly Ser Cys Val Trp Ala Arg Lys Asn Asn Lys Arg Lys Lys Asp
                20                  25                  30

Phe Asn Ala Gly Trp Gly Ser Cys
            35                  40
```

<210> SEQ ID NO 19
<211> LENGTH: 40
<212> TYPE: PRT
<213> ORGANISM: Artificial sequence
<220> FEATURE:
<223> OTHER INFORMATION: SYNTHETIC

<400> SEQUENCE: 19

```
Asp Trp Ala Arg Ser Asn Thr Ser Arg Ser Met Asp Phe Asn Leu Gly
1               5                   10                  15

Trp Gly Ser Cys Ser Trp Ala Arg Ser Asn Asn Lys Arg Ser Lys Ala
                20                  25                  30

Phe Asn Leu Gly Trp Gly Ser Cys
            35                  40
```

<210> SEQ ID NO 20
<211> LENGTH: 40
<212> TYPE: PRT
<213> ORGANISM: Artificial sequence
<220> FEATURE:
<223> OTHER INFORMATION: SYNTHETIC

<400> SEQUENCE: 20

```
Asp Trp Ala Arg Ser Asn Thr Ser Arg Ser Met Asp Phe Asn Leu Gly
1               5                   10                  15

Trp Gly Ser Cys Arg Trp His Arg Val Lys Leu Arg Ser His Thr Glu
                20                  25                  30

Leu Asn Arg Tyr Ile Gly Ser Cys
            35                  40
```

<210> SEQ ID NO 21
<211> LENGTH: 40
<212> TYPE: PRT
<213> ORGANISM: Artificial sequence
<220> FEATURE:
<223> OTHER INFORMATION: SYNTHETIC

<400> SEQUENCE: 21

```
Asp Trp Ala Arg Ser Asn Thr Ser Arg Ser Met Asp Phe Asn Leu Gly
1               5                   10                  15
```

```
Trp Gly Ser Cys Asp Trp Ala Arg Lys Asn Asn Lys Arg Lys Met Asn
            20                  25                  30

Phe Asn Leu Gly Trp Gly Ser Cys
        35                  40
```

<210> SEQ ID NO 22
<211> LENGTH: 40
<212> TYPE: PRT
<213> ORGANISM: Artificial sequence
<220> FEATURE:
<223> OTHER INFORMATION: SYNTHETIC

<400> SEQUENCE: 22

```
Asp Trp Ala Arg Ser Asn Thr Ser Arg Ser Met Asp Phe Asn Leu Gly
1               5                  10                  15

Trp Gly Ser Cys Ala Trp Ala Arg Ser Asn Asn Ser Arg Ser Lys Ala
            20                  25                  30

Phe Asn Leu Gly Trp Gly Ser Cys
        35                  40
```

<210> SEQ ID NO 23
<211> LENGTH: 40
<212> TYPE: PRT
<213> ORGANISM: Artificial sequence
<220> FEATURE:
<223> OTHER INFORMATION: SYNTHETIC

<400> SEQUENCE: 23

```
Asp Trp Ala Arg Ser Asn Thr Ser Arg Ser Met Asp Phe Asn Leu Gly
1               5                  10                  15

Trp Gly Ser Cys Arg Trp Val Arg Val Lys Leu Arg Ser His Thr Glu
            20                  25                  30

Leu Asn Arg Tyr Ile Gly Ser Cys
        35                  40
```

<210> SEQ ID NO 24
<211> LENGTH: 40
<212> TYPE: PRT
<213> ORGANISM: Artificial sequence
<220> FEATURE:
<223> OTHER INFORMATION: SYNTHETIC

<400> SEQUENCE: 24

```
Asp Trp Ala Arg Ser Asn Thr Ser Arg Ser Met Asp Phe Asn Leu Gly
1               5                  10                  15

Trp Gly Ser Cys Arg Trp Val Arg Val Lys Leu Arg Ser His Thr Lys
            20                  25                  30

Leu Asn Arg Tyr Ile Gly Ser Cys
        35                  40
```

<210> SEQ ID NO 25
<211> LENGTH: 40
<212> TYPE: PRT
<213> ORGANISM: Artificial sequence
<220> FEATURE:
<223> OTHER INFORMATION: SYNTHETIC

<400> SEQUENCE: 25

```
Leu Leu Tyr Asn Lys Thr Phe Pro His Gly Arg Trp Ser Pro Ser Tyr
1               5                  10                  15

Pro Gly Ser Cys Val Trp Ala Arg Lys Asn Asn Lys Arg Lys Lys Asp
            20                  25                  30
```

-continued

Phe Asn Ala Gly Trp Gly Ser Cys
        35                  40

<210> SEQ ID NO 26
<211> LENGTH: 40
<212> TYPE: PRT
<213> ORGANISM: Artificial sequence
<220> FEATURE:
<223> OTHER INFORMATION: SYNTHETIC

<400> SEQUENCE: 26

Leu Leu Tyr Asn Lys Thr Phe Pro His Gly Arg Trp Ser Pro Ser Tyr
1               5                   10                  15

Pro Gly Ser Cys Val Trp Ala Arg Lys Asn Ser Arg Ser Lys Asp
            20                  25                  30

Phe Asn Ala Gly Trp Gly Ser Cys
        35                  40

<210> SEQ ID NO 27
<211> LENGTH: 40
<212> TYPE: PRT
<213> ORGANISM: Artificial sequence
<220> FEATURE:
<223> OTHER INFORMATION: SYNTHETIC

<400> SEQUENCE: 27

Leu Leu Tyr Asn Lys Thr Phe Pro His Gly Arg Trp Ser Pro Ser Tyr
1               5                   10                  15

Pro Gly Ser Cys Ser Trp Ala Arg Ser Asn Asn Ser Arg Ser Met Asp
            20                  25                  30

Phe Asn Leu Gly Trp Gly Ser Cys
        35                  40

<210> SEQ ID NO 28
<211> LENGTH: 40
<212> TYPE: PRT
<213> ORGANISM: Artificial sequence
<220> FEATURE:
<223> OTHER INFORMATION: SYNTHETIC

<400> SEQUENCE: 28

Leu Leu Tyr Asn Lys Thr Phe Pro His Gly Arg Trp Ser Pro Ser Tyr
1               5                   10                  15

Pro Gly Ser Cys Arg Trp Val Arg Val Lys Leu Arg Ser His Thr Glu
            20                  25                  30

Leu Asn Arg Tyr Ile Gly Ser Cys
        35                  40

<210> SEQ ID NO 29
<211> LENGTH: 40
<212> TYPE: PRT
<213> ORGANISM: Artificial sequence
<220> FEATURE:
<223> OTHER INFORMATION: SYNTHETIC

<400> SEQUENCE: 29

Leu Leu Tyr Asn Lys Thr Phe Pro His Gly Arg Trp Ser Pro Ser Tyr
1               5                   10                  15

Pro Gly Ser Cys Arg Trp Val Arg Val Lys Leu Arg Ser His Thr Lys
            20                  25                  30

Leu Asn Arg Tyr Ile Gly Ser Cys
        35                  40

<210> SEQ ID NO 30
<211> LENGTH: 40
<212> TYPE: PRT
<213> ORGANISM: Artificial sequence
<220> FEATURE:
<223> OTHER INFORMATION: SYNTHETIC

<400> SEQUENCE: 30

```
Asp Trp Ala Arg Lys Asn Asn Lys Arg Lys Met Asn Phe Asn Leu Gly
1               5                   10                  15

Trp Gly Ser Cys Asp Trp Ala Arg Lys Asn Asn Lys Arg Lys Met Asn
            20                  25                  30

Phe Asn Leu Gly Trp Gly Ser Cys
            35                  40
```

<210> SEQ ID NO 31
<211> LENGTH: 40
<212> TYPE: PRT
<213> ORGANISM: Artificial sequence
<220> FEATURE:
<223> OTHER INFORMATION: SYNTHETIC

<400> SEQUENCE: 31

```
Ala Trp Ala Arg Ser Asn Asn Ser Arg Ser Lys Ala Phe Asn Leu Gly
1               5                   10                  15

Trp Gly Ser Cys Ala Trp Ala Arg Ser Asn Asn Ser Arg Ser Lys Ala
            20                  25                  30

Phe Asn Leu Gly Trp Gly Ser Cys
            35                  40
```

<210> SEQ ID NO 32
<211> LENGTH: 40
<212> TYPE: PRT
<213> ORGANISM: Artificial sequence
<220> FEATURE:
<223> OTHER INFORMATION: SYNTHETIC

<400> SEQUENCE: 32

```
Arg Trp Val Arg Val Lys Leu Arg Ser His Thr Glu Leu Asn Arg Tyr
1               5                   10                  15

Ile Gly Ser Cys Arg Trp Val Arg Val Lys Leu Arg Ser His Thr Glu
            20                  25                  30

Leu Asn Arg Tyr Ile Gly Ser Cys
            35                  40
```

<210> SEQ ID NO 33
<211> LENGTH: 40
<212> TYPE: PRT
<213> ORGANISM: Artificial sequence
<220> FEATURE:
<223> OTHER INFORMATION: SYNTHETIC

<400> SEQUENCE: 33

```
Ser Trp Ala Arg Ser Asn Asn Lys Arg Ser Lys Ala Phe Asn Leu Gly
1               5                   10                  15

Trp Gly Ser Cys Ser Trp Ala Arg Ser Asn Asn Lys Arg Ser Lys Ala
            20                  25                  30

Phe Asn Leu Gly Trp Gly Ser Cys
            35                  40
```

<210> SEQ ID NO 34
<211> LENGTH: 40

<212> TYPE: PRT
<213> ORGANISM: Artificial sequence
<220> FEATURE:
<223> OTHER INFORMATION: SYNTHETIC

<400> SEQUENCE: 34

Arg Trp His Arg Val Lys Leu Arg Ser His Thr Glu Leu Asn Arg Tyr
1               5                   10                  15

Ile Gly Ser Cys Arg Trp His Arg Val Lys Leu Arg Ser His Thr Glu
            20                  25                  30

Leu Asn Arg Tyr Ile Gly Ser Cys
        35                  40

<210> SEQ ID NO 35
<211> LENGTH: 40
<212> TYPE: PRT
<213> ORGANISM: Artificial sequence
<220> FEATURE:
<223> OTHER INFORMATION: SYNTHETIC

<400> SEQUENCE: 35

Arg Trp Val Arg Val Lys Leu Arg Ser His Thr Lys Leu Asn Arg Tyr
1               5                   10                  15

Ile Gly Ser Cys Arg Trp Val Arg Val Lys Leu Arg Ser His Thr Lys
            20                  25                  30

Leu Asn Arg Tyr Ile Gly Ser Cys
        35                  40

<210> SEQ ID NO 36
<211> LENGTH: 40
<212> TYPE: PRT
<213> ORGANISM: Artificial sequence
<220> FEATURE:
<223> OTHER INFORMATION: SYNTHETIC

<400> SEQUENCE: 36

Val Trp Ala Arg Lys Asn Asn Lys Arg Lys Lys Asp Phe Asn Ala Gly
1               5                   10                  15

Trp Gly Ser Cys Val Trp Ala Arg Lys Asn Asn Lys Arg Lys Lys Asp
            20                  25                  30

Phe Asn Ala Gly Trp Gly Ser Cys
        35                  40

<210> SEQ ID NO 37
<211> LENGTH: 40
<212> TYPE: PRT
<213> ORGANISM: Artificial sequence
<220> FEATURE:
<223> OTHER INFORMATION: SYNTHETIC

<400> SEQUENCE: 37

Val Trp Ala Arg Lys Asn Asn Ser Arg Ser Lys Asp Phe Asn Ala Gly
1               5                   10                  15

Trp Gly Ser Cys Val Trp Ala Arg Lys Asn Asn Ser Arg Ser Lys Asp
            20                  25                  30

Phe Asn Ala Gly Trp Gly Ser Cys
        35                  40

<210> SEQ ID NO 38
<211> LENGTH: 40
<212> TYPE: PRT
<213> ORGANISM: Artificial sequence
<220> FEATURE:

<223> OTHER INFORMATION: SYNTHETIC

<400> SEQUENCE: 38

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
        35                  40

<210> SEQ ID NO 39
<211> LENGTH: 40
<212> TYPE: PRT
<213> ORGANISM: Artificial sequence
<220> FEATURE:
<223> OTHER INFORMATION: SYNTHETIC

<400> SEQUENCE: 39

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
        35                  40

<210> SEQ ID NO 40
<211> LENGTH: 40
<212> TYPE: PRT
<213> ORGANISM: Artificial sequence
<220> FEATURE:
<223> OTHER INFORMATION: SYNTHETIC

<400> SEQUENCE: 40

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
        35                  40

<210> SEQ ID NO 41
<211> LENGTH: 40
<212> TYPE: PRT
<213> ORGANISM: Artificial sequence
<220> FEATURE:
<223> OTHER INFORMATION: SYNTHETIC

<400> SEQUENCE: 41

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
        35                  40

<210> SEQ ID NO 42
<211> LENGTH: 40
<212> TYPE: PRT
<213> ORGANISM: Artificial sequence
<220> FEATURE:
<223> OTHER INFORMATION: SYNTHETIC

<400> SEQUENCE: 42

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
            35                  40

<210> SEQ ID NO 43
<211> LENGTH: 40
<212> TYPE: PRT
<213> ORGANISM: Artificial sequence
<220> FEATURE:
<223> OTHER INFORMATION: SYNTHETIC

<400> SEQUENCE: 43

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
            35                  40

<210> SEQ ID NO 44
<211> LENGTH: 40
<212> TYPE: PRT
<213> ORGANISM: Artificial sequence
<220> FEATURE:
<223> OTHER INFORMATION: SYNTHETIC

<400> SEQUENCE: 44

Leu Leu Tyr Asn Lys Thr Phe Pro His Gly Arg Trp Ser Pro Ser Tyr
1               5                   10                  15

Pro Gly Ser Cys Leu Leu Tyr Asn Lys Thr Phe Pro His Gly Arg Trp
            20                  25                  30

Ser Pro Ser Tyr Pro Gly Ser Cys
            35                  40

<210> SEQ ID NO 45
<211> LENGTH: 40
<212> TYPE: PRT
<213> ORGANISM: Artificial sequence
<220> FEATURE:
<223> OTHER INFORMATION: SYNTHETIC

<400> SEQUENCE: 45

Asp Trp Ala Arg Ser Asn Thr Ser Arg Ser Met Asp Phe Asn Leu Gly
1               5                   10                  15

Trp Gly Ser Cys Val Trp Ala Arg Lys Asn Asn Lys Arg Lys Lys Asp
            20                  25                  30

Phe Asn Ala Gly Trp Gly Ser Cys
            35                  40

<210> SEQ ID NO 46
<211> LENGTH: 40
<212> TYPE: PRT
<213> ORGANISM: Artificial sequence
<220> FEATURE:
<223> OTHER INFORMATION: SYNTHETIC

<400> SEQUENCE: 46

Asp Trp Ala Arg Ser Asn Thr Ser Arg Ser Met Asp Phe Asn Leu Gly
1               5                   10                  15

Trp Gly Ser Cys Arg Trp His Arg Val Lys Leu Arg Ser His Thr Glu
            20                  25                  30

Leu Asn Arg Tyr Ile Gly Ser Cys
            35                  40

<210> SEQ ID NO 47
<211> LENGTH: 40
<212> TYPE: PRT
<213> ORGANISM: Artificial sequence
<220> FEATURE:
<223> OTHER INFORMATION: SYNTHETIC

<400> SEQUENCE: 47

Arg Trp His Arg Val Asp Leu Arg Ser His Thr Glu Leu Pro Arg Tyr
1               5                   10                  15

Ile Gly Ser Cys Arg Trp His Arg Val Asp Leu Arg Ser His Thr Glu
            20                  25                  30

Leu Pro Arg Tyr Ile Gly Ser Cys
            35                  40

<210> SEQ ID NO 48
<211> LENGTH: 40
<212> TYPE: PRT
<213> ORGANISM: Artificial sequence
<220> FEATURE:
<223> OTHER INFORMATION: SYNTHETIC

<400> SEQUENCE: 48

Arg Trp His Arg Val Asp Leu Arg Ser His Thr Glu Leu Pro Arg Tyr
1               5                   10                  15

Ile Gly Ser Cys Val Trp Ala Arg Lys Asn Asn Lys Arg Lys Lys Asp
            20                  25                  30

Phe Asn Ala Gly Trp Gly Ser Cys
            35                  40

<210> SEQ ID NO 49
<211> LENGTH: 40
<212> TYPE: PRT
<213> ORGANISM: Artificial sequence
<220> FEATURE:
<223> OTHER INFORMATION: SYNTHETIC

<400> SEQUENCE: 49

Arg Trp His Arg Val Asp Leu Arg Ser His Thr Glu Leu Pro Arg Tyr
1               5                   10                  15

Ile Gly Ser Cys Ala Trp Ala Arg Ser Asn Asn Ser Arg Ser Lys Ala
            20                  25                  30

Phe Asn Leu Gly Trp Gly Ser Cys
            35                  40

<210> SEQ ID NO 50
<211> LENGTH: 40
<212> TYPE: PRT
<213> ORGANISM: Artificial sequence
<220> FEATURE:
<223> OTHER INFORMATION: SYNTHETIC

<400> SEQUENCE: 50

Arg Trp His Arg Val Asp Leu Arg Ser His Thr Glu Leu Pro Arg Tyr
1               5                   10                  15

Ile Gly Ser Cys Arg Trp His Arg Val Lys Leu Arg Ser His Thr Glu
            20                  25                  30

```
Leu Asn Arg Tyr Ile Gly Ser Cys
        35                  40

<210> SEQ ID NO 51
<211> LENGTH: 40
<212> TYPE: PRT
<213> ORGANISM: Artificial sequence
<220> FEATURE:
<223> OTHER INFORMATION: SYNTHETIC

<400> SEQUENCE: 51

Arg Trp His Arg Val Asp Leu Arg Ser His Thr Glu Leu Pro Arg Tyr
1               5                   10                  15

Ile Gly Ser Cys Arg Trp Val Arg Val Lys Leu Arg Ser His Thr Glu
            20                  25                  30

Leu Asn Arg Tyr Ile Gly Ser Cys
        35                  40

<210> SEQ ID NO 52
<211> LENGTH: 40
<212> TYPE: PRT
<213> ORGANISM: Artificial sequence
<220> FEATURE:
<223> OTHER INFORMATION: SYNTHETIC

<400> SEQUENCE: 52

Arg Trp His Arg Val Asp Leu Arg Ser His Thr Glu Leu Pro Arg Tyr
1               5                   10                  15

Ile Gly Ser Cys Arg Trp Val Arg Val Lys Leu Arg Ser His Thr Lys
            20                  25                  30

Leu Asn Arg Tyr Ile Gly Ser Cys
        35                  40
```